United States Patent [19]

Giese

[11] 4,282,287

[45] Aug. 4, 1981

[54] BIOCHEMICAL AVIDIN-BIOTIN MULTIPLE-LAYER SYSTEM

[76] Inventor: Roger W. Giese, 56 Oakland Ave., Quincy, Mass. 02170

[21] Appl. No.: 114,898

[22] Filed: Jan. 24, 1980

[51] Int. Cl.³ .......................... B32B 5/16; B32B 9/00
[52] U.S. Cl. ....................................... 428/407; 427/2;
427/214; 427/220; 427/222; 427/331; 427/399;
427/400; 427/414; 428/478.2; 428/403
[58] Field of Search .................. 427/2, 214, 399, 220,
427/400, 222, 414, 352, 331; 435/7, 188;
422/57; 428/403, 407, 478.2

[56] References Cited

U.S. PATENT DOCUMENTS

| 4,132,528 | 1/1979 | Eikenberry et al. ................ 422/57 |
| 4,134,792 | 1/1979 | Boguslaski et al. ................ 435/7 |
| 4,168,300 | 9/1979 | Andersson et al. ................ 424/12 |

OTHER PUBLICATIONS

Costello et al., "Enhancement of Immune Cellular Agglutination by Use of An Avidin–Biotin System", Clinical Chemistry, vol. 25, No. 9, 1979.

Jasiewicz et al., "Selective Retrieval of Biotin–Labeled Cells Using Immobilized Avidin", Experimental Cell Research 100 (1976).

Bayer et al., "The Avidin–Biotin Complex as a Tool in Molecular Biology", Trends in Biochemical Science, 3, N257, Nov. 1978.

Primary Examiner—Ronald H. Smith
Assistant Examiner—S. L. Childs
Attorney, Agent, or Firm—Richard P. Crowley

[57] ABSTRACT

A multiple-layer process for applying, in alternate, successive layers, the protein, avidin, and a biotin-containing extender material to a solid surface to modify the properties of the surface and to the multiple-layer product so prepared.

28 Claims, 2 Drawing Figures

LAYERING OF POLYMER BEADS
WITH AVIDIN AND BIOTIN REAGENTS.
THE LAYERING CYCLE
(THE NUMBER OF AVIDIN LAYERS)
IS INDICATED BY n

BEADS (AMINOPOLYACRYLAMIDE)

↓ 1. BIOTIN NHS ESTER
  2. AVIDIN

BEADS-BIOTIN-AVIDIN  $\xrightarrow{BHRPO}$  COLOR$_{n=1}$
       (n=1)

↓ [1. BRNASE]
  [2. AVIDIN ]  n = 2, 3, 4, 5

BEADS BIOTIN AVIDIN  $\xrightarrow{BHRPO}$  COLOR$_{n=2,3,4,5}$

[BRNASE-AVIDIN]  n = 2, 3, 4, 5

BIOCHEMICAL AVIDIN-BIOTIN MULTIPLE-LAYER SYSTEM

BACKGROUND OF THE INVENTION

Avidin is a protein found in egg whites and contains four subunits. Biotin is a stable, water-soluble vitamin. Biotin and avidin interact specifically under mild and certain harsh conditions to form a strong, stable, avidin-biotin complex in which each of the four subunits of avidin bind a biotin molecule. This binding persists when biotin is attached by means of its carboxyl group to another molecule, or when avidin is attached to another molecule. For example, biotin may be secured or attached to molecules on the surface of a cell or to anticellular antibodies which have been reacted onto a cell, and then subsequently is reacted with a ferritin-avidin conjugate, to provide a method for localization studies in affinity cytochemistry (see, for example, *Trends in Biochemical Science,* 3, N257 (1978), hereby incorporated by reference). Biotinyl-antibody and conjugated avidin products (with fluorescein, rhodamine, ferritin or horse radish peroxidase) are offered commercially, to provide investigators with reagents for studying biochemical and immunochemical structures or processes; for example, the location or extent of cell-surface substances.

A modified avidin-biotin system has been employed to enhance immune cellular agglutination of erythrocytes (see *Clinical Chemistry,* 25, No. 9, 1572 (1979), hereby incorporated by reference). Biotin or caproylamidobiotin was either attached directly to the cells or indirectly using biotin or caproylamidobiotin-anticellular antibody. The addition of avidin then achieved agglutination, and a biotin or caproylamidobiotin-conjugated macromolecule was added as an extender in conjunction with more avidin, to enhance the agglutination.

SUMMARY OF THE INVENTION

My invention relates to a process of preparing an avidin-biotin, multiple-layer system ("layering") and to the system so prepared. In particular, my invention concerns a process of preparing a multiple-layer system involving repetitive, specific, monomolecular or monoparticulate layers of avidin and biotin-containing substances, to the multiple-layer system so prepared, and to the use of the system and process to change surface properties.

My multiple-layer process and multiple-layer product comprise avidin, biotin (and any derivatives, analogs or substitutes of these which still comprise an analogous binding interaction) and a material referred to as an extender. An extender is defined as a molecule or substance to which one or more biotins have been attached such that these biotins still undergo binding by avidin. The extender useful in my invention may comprise those extenders which are described in the *Clinical Chemistry* publication, supra, or other biotin-modified molecules or particles. Typical and specific extenders include, but are not limited to: fibrinogen, albumin, succinylated polylysine and ribonuclease appropriately modified with biotin or biotin derivatives. These extenders may be used separately or in combination or as separate layers of different extenders as desired.

Typical examples of avidin derivatives include, but are not limited to: succinyl avidin, ferritin avidin, enzyme avidin and cross-linked avidin. A typical example of an avidin analog is the bacterial biotin-binding protein, streptavidin, whose physical and chemical characteristics are similar to those of avidin. A typical example of an avidin substitute is a ligand-binding substance with multiple ligand-binding sites, such as a lectin, antibody, protein A (purified or cell-bound), etc., in conjunction with an appropriate ligand (lectins bind sugar ligands, antibodies bind hapten or antigenic determinant ligands, and protein A binds $F_c$ ligand). Typical examples of biotin derivatives include, but are not limited to: caproylamidobiotin and biocytin. Typical examples of biotin analogs are desthiobiotin and biotin sulfone and of biotin substitutes are ligands for appropriate substitute binding substances; that is, sugars, haptens or antigenic determinants, $F_c$, for lectins, antibodies, protein A, etc., as defined above.

The multiple-layer process is defined as the successive, repetitive attachment of avidin and extenders to a surface to build up alternate layers of each. The initial step could be attachment of either one of these reagents (covalently or noncovalently) to a surface, or direct firm attachment of biotins to the surface. For example, where the surface is, firstly, covalently bonded with biotin, then layering would be achieved by repetition of the following sequence of steps (a-d) to build up successive layers of avidin and extender: (a) add avidin; (b) wash away unbound avidin; (c) add extender; and (d) wash away unbound extender, and then, optionally, perform a derivatization reaction; for example, cross-linking or modifying of functional groups, in between any of the above steps and/or after all the layers have been developed to change the properties further; for example, provide a more complete coverage of the surface, more stability, different functional groups, etc. In my layering process, primarily or exclusively monomolecular or monoparticulate layers of avidin and extender (a single extender or various extender materials may be used in a given multiple-layer process) are built up on a surface, but the process may be relaxed by omitting washing steps, thereby possibly mixing in coverage with multimolecular or multiparticulate species.

Any conceivable surface may be employed, whether biological, nonbiological, organic, inorganic, or a combination of any of these, any whether formulated or existing as molecules, molecular aggregates, particles, strands, precipitates, gels, sheets, tubing, spheres, containers, capillaries, pads, slices, film, etc. (for example, cells, tissue, tumors, organelles, proteins, polymers, elastomers, microorganisms, viruses, nucleic acids, plastics, resins, polysaccharides, silica or silica-based materials, carbon, metals, inorganic salts, chromatographic supports, test tubes, etc.); provided only that some component of the layering system can be attached firmly to initiate the process. The attachment of avidin to biotin or extender can proceed under mild conditions (for example, aqueous solvents and room temperature).

The basic concept of developing repetitive, specific, alternate, monomolecular or monoparticulate layers on a surface is unprecedented. My "layering" system bears no relation to conventional surface-treatment processes, such as painting, because of the latter's gross number of molecules and variable layer thickness involved, the poorly controlled nonspecific nature of the process, the complex and often crude nature of many of the components, and the major effect achieved by the first or second layer with subsequent layers typically leading to equivalent or diminished returns.

My "layering" process constitutes a new process at the molecular or monoparticulate level, with an opportunity to develop specifically and to control molecular distances and constructions, with exact choices of components. In my process, the first layer is merely a beginning, and the overall layering process involves a careful and well-defined building up and constructing of an array of molecules or particles on a given surface in an exact and sophisticated manner, and with great variety, if so desired. The process and product are characterized by a unique array of characteristics which requires all of the aspects mentioned (repetitive, specific, alternate monomolecular or monoparticulate layers), and which qualitatively and/or quantitatively can differ vastly from the properties or effects achieved by the initial layer or even initial several layers.

Overall my layering avidin-biotin system offers significant advantages in terms of the overall accessibility, stability, cost, size, solubility and multiple binding sites of its components, and the analogs, derivatives and substitutes for avidin and biotin are within the scope of my layering system.

A wide variety of problems associated with surfaces are now subject to a new mode of attack with my multiple-layer process and product. For example, my process may be used to change the adsorptive, functional, catalytic, reactivity, transport, adhesive, stability, charge, toxicity, biological foreignness, frictional, electrical potential, chromatographic, pore size, rigidity, wettability, reflective, conductance, energy transfer, immunogenic, roughness, hardness, etc. properties of a surface; to stabilize the inherent properties of a surface; to determine distances between sites (for example, once the distance is layered, it is shut off from further layering, or signal molecules, such as a fluorescence molecule and a fluorescence quencher, or interacting spin labels, could be used to reveal when the layers from the sites reach a certain proximity); to establish connections between sites on the same or different surfaces; to cause movement of sites on or between surfaces and, therefore, of the surfaces themselves; to disrupt a surface; to provide an exact distance between functional molecules or substances on a surface or between different surfaces; to create, study, optimize or otherwise change an interaction or binding or disruption between surfaces or between surfaces and some other substances or molecules; to provide a special microenvironment or access or protection, etc. for functional molecules or substances on surfaces; to allow larger or more complex particles to be developed by starting with a core molecule or particle and building up layers; and to allow the development of exceedingly small circuitry.

Specific examples of some uses would be to increase the extent of attachment of an enzyme, antibody, coenzyme, fluorophor, radionuclide, drug or other special atom or molecule to a surface for enhancing immunoassay, affinity chromatography, therapy, enzyme engineering, solar-energy conversion, catalysis, etc.; to reduce the pore sizes of a dialysis or filtration surface; to change retention characteristics; to change the pore size and/or surface properties of silica or silica-based particles for chromatographic or adsorption-control purposes; to exert or to enhance a physical, chemical or biological activating, inhibiting, disrupting, toxicity or killing action against a desirable or undesirable surface, such as a tumor cell, infectious microorganism, diseased tissue or disease-causing agent; to change the foreignness (for example, immunogenicity) of host tissue for reduced rejection by donor or decreased graft-vs.-host response in tissue-transplant procedures; to reduce or eliminate the foreignness of artificial tissue or implant materials (for example, reduced thrombogenic action, reduced immune or phagocytic response) in artificial-organ or-tissue operations (for example, involving plastics and other polymers, etc.); to constitute a glue or adhesive for joining tissues to other tissues or artificial surfaces; to fix tissues; to preserve foods; to use in or achieve molecular surgery; to create channels or reservoirs for reactive molecules or products; to bring together drugs, enzymes, energy-transport molecules, etc. into an arrangement and structure which optimizes their performance and action; and to create novel physiological-transport agents. Other uses of my multiple-layer process and product would be apparent to a person skilled in the art.

My layering system will be demonstrated employing the process with certain caproylamidobiotin ribonuclease found particularly to be effective as an extender.

An appropriate model surface and signal extender are used to demonstrate my layering process. Essentially, nonadsorbing conditions for all reagents were achieved in order to avoid nonspecific effects. An aminoethylpolyacrylamide as a surface material and a signal extender were used; that is, horse radish peroxidase modified successively with hexanediamine/carbodiimide, caproylamidobiotin NHS and succinic anhydride.

my process includes not only the basic layering process, but also "amplification layering", to achieve relatively increasing amounts of corresponding substances in successive layers during this process. Such amplification layering is essential for many of the potential benefits and opportunities of layering to be realized fully. For example, a general, basic problem with surface treatments involving coatings of one to several molecules is that complete coverages are not achieved. An amplification-layering process can provide complete surface coverage, because of its ability to continue to expand the surface coating in all available directions.

For the purpose of illustration only, my multiple-layer process and product will be described with reference to certain specific embodiments; however, it is recognized that those persons skilled in the art may make certain changes and modifications, all within the scope and intent of my invention.

DESCRIPTION OF THE EMBODIMENTS

Figures 1, 2:
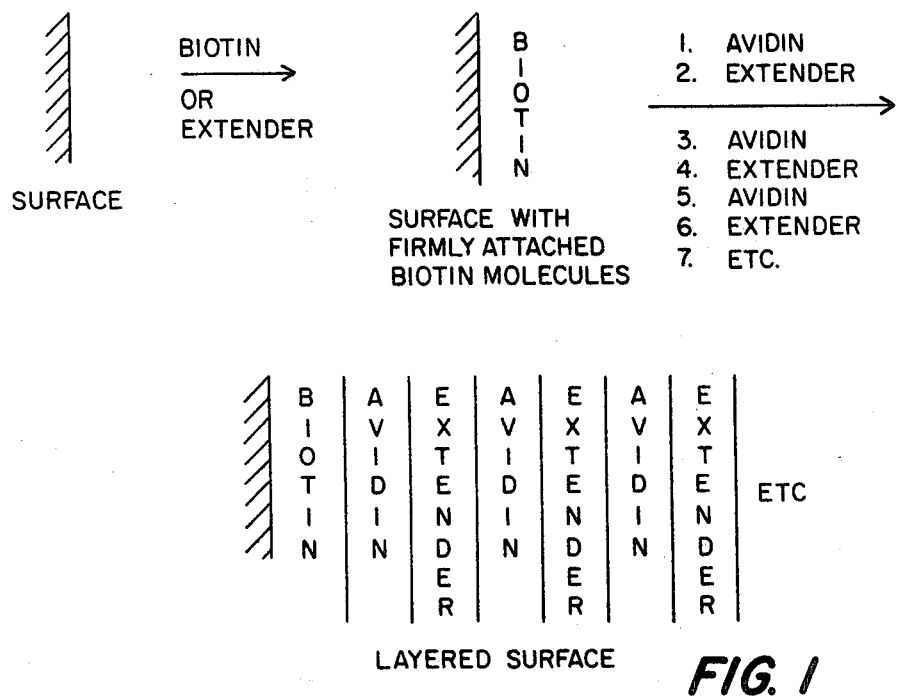
FIG. 1 is a schematic illustration of the multiple-layer process and layering system of my invention.
FIG. 2 is a schematic illustration of a specific multiple-layer process and layering system of my invention.

FIG. 1 is a schematic illustration of a multiple-layer process and layering system of my invention, wherein the biotin is covalently bonded directly to the illustrative surface in the first step, avidin is applied in the next step, and extender (a material to which biotin groups are attached as defined previously) is added, followed by repetitive further additions of avidin and noncovalent extender with intermediate washing steps to remove excess reagents.

It is recognized that the layers may be mixed, that various extenders and forms of avidin (and any derivatives, analogs or substitutes of these) may be used separately, concurrently, intermittently, etc. in a given layering process, that the layering process may result in constant, increasing or decreasing amounts of corresponding substances in successive layers, and that the layers may proceed in the form of molecular and/or particulate sheets, clumps, spheres, patches, rods, tubes, etc. from the initiation sites on the surface.

FIG. 2 shows a schematic illustration of a specific, multiple-layer process and product, wherein the surface comprises polyacrylamide particles containing reactive alkylamine groups, which then was modified by reaction with a layer of biotin-NHS esters. The modified surface was then coated with alternating successive layers of avidin and a biotin-ribonuclease extender material, illustrated as five successive layers, to modify the surface of the particles. The extent of avidin attachment in each layering step was monitored by adding an aliquot biotin-horse radish peroxidase (BHRPO) to each avidin layer treatment. The BHPRO served as a signal extender. Appropriate washing and control steps and treatment were carried out. The HRPO color at 500 nanometers was measured after each avidin layering step as a measure of the amount of avidin (most specifically, available avidin-binding sites for BHRPO), and the layering process was found to generate increasing amounts of avidin with each avidin layer (amplification layering), one of the three possibilities (constant, decreasing or increasing) cited earlier. The color-vs.-number-of-layers is as shown in Table 1.

TABLE I

| | Absorbance 500 nm (color) vs. Number of Layering Cycles | |
|---|---|---|
| No. of Layers Avidin (n) | Color Absorbance | Absorbance Difference Values |
| 1 | .746 | |
| 2 | .832 | .086* |
| 3 | .964 | .132 |
| 4 | 1.124 | .160 |
| 5 | 1.379 | .255 |

*0.832 − 0.746 = 0.086

In order to illustrate more fully the nature of the invention and the manner of practicing the same, the following Example is presented:

EXAMPLE

Materials

1. Affigel-701 from Bio-Rad—an aminoethyl derivative of polyacrylamide in a bead form, 1–3 microns in diameter. The beads were provided in an aqueous suspension at $25 \pm 3$ $\mu$/mol of amine groups/ml.

2. Phosphate buffered saline (PBS)—an 0.01 M sodium phosphate, 0.15 M sodium chloride, pH 7.4.

3. Avidin—dissolved in PBS at 0.1 mg/ml based on weight.

4. Wash buffer—The buffer used for all washing steps was PBS containing bovine serum albumin (BSA) at 0.02% wt and Tween-20 surfactant at 0.05% wt.

5. HRPO substrate—was freshly prepared by dissolving phenol (100 mg) and 4-aminoantipyrine (16.2 mg) in a solution composed of 0.5 M $Na_2HPO_4$(2 ml), 0.5 M $KH_2PO_4$(18 ml), water (180 ml) and 30% $H_2O_2$(20 $\mu$l).

6. Silanized glass tubes—Disposable borosilicate glass tubes (12×75 mm) were silanized by filling with a 2% solution of chlorotrimethylsilane in benzene. The silanizing reagent was decanted after ½ hour, the tubes rinsed with acetone and air-dried.

7. Biotin NHS ester (biotin N-hydroxysuccinimide ester)—was prepared as defined in Jasiewicz, M. M., Schoenberg, D. R., and Mueller, G. C., Exp. Cell Res. 100, 213 (1978), hereby incorporated by reference.

8. Caproylamidobiotin-NHS and caproylamidobiotin-RNase (BRNase)—were prepared as defined previously (Costello, S. M. Felix, R. T. and Giese, R. W., Clin. Chem. 25, 1572 (1979), herein incorporated by reference).

9. BHRPO horse radish peroxidase (Worthington Biochemical)—10 mg were dissolved in 1 ml of water. This was added to a solution consisting of 1,6-hexanediamine (116 mg), 0.2 M sodium pyrophosphate (2.0 ml), water (5.0 ml) and sufficient concentrated HCl to bring the pH to 5.5. A solid water-soluble carbodiimide, 1-ethyl-3-(3-dimethylaminopyroyl) carbodiimide (EDC) was added to the gently mixed solution at room temperature. Three separate additions of 190 mg each were made over a 1-hour period. 1½ hours after the first addition, the contents of the beaker were placed in a dialysis bag and dialyzed against 4×400 ml of PBS (pH=7.4). An aliquot (10 ml) from the dialysis bag was added to a solution of caproylamidobiotin-NHS ester (4.1 mg) in N,N-dimethylformamide (DMF) (0.1 ml). This solution was allowed to stand at room temperature for 1½ hours and was then dialyzed against 4×400 ml of PBS (pH=7.4).

An aliquot (2 ml) of the above was placed in a dialysis bag and dialyzed against $NaHCO_3$ (1 M) for 24 hours. The sample (at pH=8.6) was removed from the bag, placed in a small beaker with a magnetic mixer and reacted with 4×10 $\mu$l aliquots (15 minutes apart) of succinic anhydride (40 mg) in DMF (1 ml). The sample was placed in a dialysis bag 15 minutes after the last addition and dialyzed against 4×400 ml of PBS (pH=7.4).

Assuming 100% recovery of enzyme, the concentration of biotinyl-HRPO (BHRPO) would be approximately 0.8 mg/ml. It migrated electrophoretically (cellulose acetate, pH 8.6 buffer) in a manner similar to native enzyme (although the band was more diffuse).

10. Biotin-beads suspension—Affigel-701 (5.0 ml, about 125 $\mu$mol of amine groups) was added to PBS (5.0 ml). This suspension was vortexed 10 seconds, and biotin NHS ester (43 mg, 125 $\mu$mol) dissolved in DMF (0.1 ml) was added all at once. The reaction mixture was allowed to mix end over end for 2 hours at room temperature.

The beads were packed by centrifugation and the supernatant discarded. The bead pellet was resuspended in PBS and washed with 4×20 ml of PBS. The beads (biotin beads) were finally suspended in PBS (20 ml) containing $NaN_3$ (0.02%).

Layering of Biotin Beads

Aliquots (50 ul) of biotin-bead suspension (magnetically mixing) were placed in 12×75 mm silanized glass tubes. Each tube was treated with avidin (0.1 mg in 1 ml PBS) for 10 minutes at room temperature. The beads were then centrifuged and the supernatants collected. The beads were washed X3 with wash buffer.

A layer was applied to the avidin-biotin beads by suspending them in 1 ml of caproylamidobiotin RNase (BRNase approximately 60 $\mu$g/ml) for 10 minutes. The beads were then spun and the supernatants collected. The beads were then washed X3 with wash buffer. The newly added biotin residues were next reacted with avidin as above. The sequence of avidin followed by BRNase, with intermittent washing steps, was repeated four more times. This process is set forth in FIG. 2.

Functional biotin binding sites on avidin-biotin beads (or layered beads) were detected by suspending aliquots of the beads after each avidin step in 200 μl of BHRPO (2 μg/ml) in PBS for 30 minutes. Unbound enzyme was removed by threefold washing with wash buffer. Bound enzyme was detected by addition of HRPO substrate (4.5 ml). After 30 minutes at room temperature, the tubes were chilled in an ice bath for 5 minutes and then spun. The supernatants were decanted and diluted with PBS (4.5 ml).

The $A_{500}$ values of the diluted substrate solutions were measured on a Gilford 240 using water as a reference, and are given in Table I. As seen, the amount of functional enzyme on the beads is greater with each cycle of layering, and the rate of increase (giving by the difference values) also is increasing significantly as the layering proceeds; for example, the value 0.255 between layers 4 and 5 is 2.96 times greater than the value 0.086 between layers 1 and 2. This demonstrates the usefulness of layering for placing functional enzyme on a surface, increasing the amount of functional enzyme on a surface, and achieving an increasing rate of layering for the enzyme; that is, a relative increase in the amount of enzyme attached with each successive layer.

Avidin and some of the ligand binding proteins which may be employed in the practice of my invention are set forth in Table II.

TABLE II

Avidin and Some Other Ligand-binding Proteins

| Protein | Ligand | Affinity (Ka) | Usual No. of binding sites |
|---|---|---|---|
| Lectins | Simple sugars | $10^3$–$10^4$ | 4 |
|  | membrane sites | $10^6$–$10^7$ |  |
| Protein A (S. aureus) | $F_c$ of IgG | $10^7$ | 4 |
| Antibodies | Haptens | $10^5$–$10^{11}$ | 2 |
|  | Antigenic determinants | $10^5$–$10^{11}$ | 2 |
| Avidin | Biotin | $10^{15}$ | 4 |
| Streptavidin | Biotin | — | 4 |

Having thus described my invention, What I claim is:

1. A process of modifying the surface properties of a surface, which process comprises:
applying alternative, monomolecular, successive layers of first and and second materials to a surface to be modified, the first material comprising avidin and the second material comprising a noncovalent, biotin-modified extender, one of the materials reacted to the surface, and, thereafter, at least one additional layer of each of the first and second materials alternated, secured and reacted to the underlying layer, to provide a surface with the first or second material as the top surface layer thereon.

2. The process of claim 1 wherein the top surface of the process comprises the second extender material.

3. The process of claim 1 wherein the first material comprises a modified avidin adapted to react with the second extender material through the avidin portion of the modified material.

4. The process of claim 1 which includes pretreating the surface with a monomolecular layer of biotin, and wherein the first avidin material is applied over and secured to the biotin layer.

5. The process of claim 1 which includes:
(a) applying a monomolecular layer of biotin and covalently binding the biotin to the surface;
(b) applying and reacting a monomolecular layer of avidin to the biotin layer; and
(c) applying and reacting a monomolecular layer of a biotin extender material to the avidin layer.

6. The process of claim 5 which includes:
(a) applying another layer of avidin; and
(b) applying another layer of the biotin extender material to the other layer of avidin.

7. The process of claim 1, which process includes varying the concentration of the first or second material in the alternate, successive layers.

8. The process of claim 7 which includes increasing the concentration of the alternate, successive layers of the first and second materials.

9. The process of claim 7 which includes decreasing the concentration of the alternate, successive layers of the first and second materials.

10. The process of claim 1 which includes applying alternate, successive layers of approximately the same stochiometric concentration.

11. The process of claim 1 wherein the surface comprises a polymeric surface.

12. The process of claim 11 wherein the surface comprises the surface of finely-divided, polyacrylamide, polymer particles.

13. The process of claim 11 wherein the surface comprises erythrocytes.

14. The process of claim 1 wherein the surface comprises the surface of amino polyacrylamide particles, and the process comprises applying a layer of biotin-NHS esters to the surface of the particles, and, thereafter, applying successive, alternate, monomolecular layers of avidin and biotin-ribonuclease material.

15. The process of claim 1 wherein the first and second materials comprise three or more layers.

16. The process of claim 1 wherein the first and second materials comprise two monomolecular layers.

17. The process of claim 1 wherein each layer of the materials is monomolecular or monoparticulate in thickness.

18. The process of claim 1 which includes reacting at least one of the avidin layers with a biotin-horse radish peroxidase or a biotin ribonuclease as a signal extender.

19. The layering system produced by the process of claim 1.

20. The layering system produced by the process of claim 14.

21. A monomolecular-layering process of modifying the surface properties of a substrate surface of a polymer, which process comprises:
(a) applying a layer of a biotin-N-hydroxysuccinimide ester as a biotin-extender material to the surface of a polymer, to react the biotin-N-hydroxysuccinimide to the surface of the polymer;
(b) washing the polymer surface to remove unreacted biotin-N-hydroxysuccinimide;
(c) applying a layer of avidin to the washed polymer surface, to react the avidin with the biotin-N-hydroxysuccinimide extender material;
(d) washing the reacted surface to remove unreacted avidin;
(e) applying to the washed avidin surface a layer of a caproylamidobiotin NHS or RNase as a biotin-extender material;
(f) washing the reacted surface to remove unreacted biotin-extender material; and (g) recovering the polymer having multiple layers, with the top layer composed of a biotin-extender material.

22. The process of claim 21 which includes:
(a) applying avidin to the washed polymer surface, to react another layer of avidin with the biotin-extender material;
(b) washing the reacted surface to remove unreacted avidin; and
(c) recovering a polymer having multiple layers, with the top layer composed of avidin.

23. The process of claim 22 which includes repeating the successive application of biotin-extender material and avidin, with intermittent wash steps, to provide a polymer surface with successive monomolecular layers of avidin and biotinextender material, with the top monomolecular layer being either avidin or a biotin-extender material.

24. The process of claim 21 wherein the polymer comprises an aminoalkyl polyacrylamide polymer.

25. The process of claim 21 which includes reacting a small amount of a biotin-peroxidase or -ribonuclease material, as a signal extender for the avidin, with at least one of the applications of the avidin.

26. The polymeric-layering system produced by the process of claim 21.

27. The polymeric-layering system produced by the process of claim 22.

28. The polymeric-layering system produced by the process of claim 23.

* * * * *